(12) United States Patent
Benes

(10) Patent No.: US 8,263,397 B2
(45) Date of Patent: Sep. 11, 2012

(54) FEMALE SPECIFIC INSECT EXPRESSION SYSTEM

(75) Inventor: Helen Benes, Little Rock, AR (US)

(73) Assignee: The Board of Trustees of the University of Arkansas, Little Rock, AR (US)

( * ) Notice: Subject to any disclaimer, the term of this patent is extended or adjusted under 35 U.S.C. 154(b) by 0 days.

(21) Appl. No.: 12/722,968

(22) Filed: Mar. 12, 2010

(65) Prior Publication Data

US 2011/0225662 A1    Sep. 15, 2011

(51) Int. Cl.
*C12N 15/00* (2006.01)
*C07H 21/04* (2006.01)
(52) U.S. Cl. .................. 435/320.1; 536/24.1
(58) Field of Classification Search ........... 435/320.1; 536/23.1, 24.1; 800/13, 21
See application file for complete search history.

(56) References Cited

U.S. PATENT DOCUMENTS

2003/0213005 A1    11/2003  Alphey et al.

FOREIGN PATENT DOCUMENTS

| WO | WO03/018827 | * | 3/2003 |
| WO | WO03018827 A2 | | 3/2003 |

OTHER PUBLICATIONS

Jinwal et al (Insect. Mol. Biol. Jun. 2006, 15(3), 301-311.*
Jinwal et al Insect. Mol. Biol. Jun. 2006, 15(3), 301-311.*
NCBI accession No. AF430247, 1-5, 2003.*
Horn et al Nature Biotech. 2003, 21, 64-70.*
Catteruccia et al., Stable Germline Transformation of the malaria mosquito *Anopheles stephensi*. Nature, vol. 405, 959-963 (2000).
Rubin et al., Genetic Transformation of *Drosophila* with Transposable Element Vectors, Science, vol. 218, Oct. 22, 1982.
Alphey, Re-engineering the sterile insect technique, Insect Biochemistry and Molecular Biology, 2002, pp. 1243-1247, vol. 32.
International Search Report and Written Opinion from related Application No. PCT/US11/28025, dated May 24, 2011, 9 pages.

* cited by examiner

*Primary Examiner* — Anoop Singh
(74) *Attorney, Agent, or Firm* — Polsinelli Shughart PC

(57) ABSTRACT

The present invention provides an insect expression system that may be used to provide biological control of pest insects and control transmission of infectious diseases transmitted to the human population by insects.

10 Claims, 6 Drawing Sheets
(6 of 6 Drawing Sheet(s) Filed in Color)

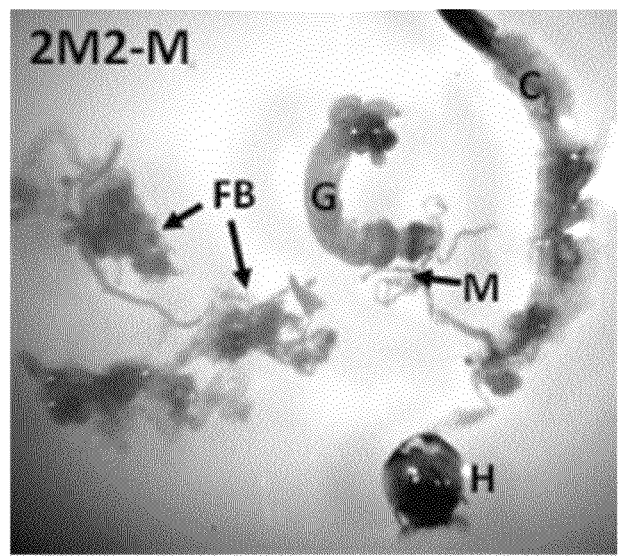
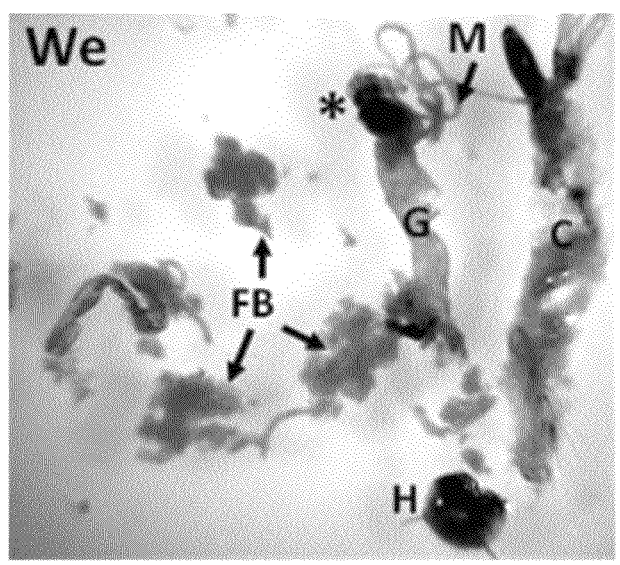

FEMALE SPECIFIC INSECT EXPRESSION SYSTEM

GOVERNMENTAL RIGHTS

This invention was made with government support under A104678 awarded by the National Institutes of Health. The government has certain rights in the invention.

FIELD OF THE INVENTION

The invention encompasses an insect expression system that directs female-specific expression in insects. The invention may be used to provide biological control of pest insects and control insect transmission of infectious diseases to the human population.

BACKGROUND OF THE INVENTION

Methods of biological control are a long-standing and potentially powerful alternative to pesticides for insect control and control of the diseases insects spread. One method currently employed for the control of insect populations is termed the "sterile insect technique" (SIT). SIT has been applied worldwide to eradicate specific populations of agricultural pests or disease vectors, including the mosquito. For the last 30 years, SIT has relied on classical genetic manipulation to generate genetic sexing strains for mass production of exclusively male insects. These males, generally sterilized by irradiation, are released into the wild in large numbers to produce ineffectual matings with wild females. As a result, there are no progeny from these wild female insects and the insect population is dramatically reduced. Irradiation of male insects, however, puts them at a competitive disadvantage with wild males.

A more desirable modification of the traditional SIT approach, called "release of insects carrying a dominant lethal" (RIDL) depends on female-specific promoter/enhancer elements to bring about female lethality by induced expression of a dominant female-specific lethal effector. In this manner, the males are not irradiated, and are reproductively competitive with wild male populations.

Female-specific expression in insects also has the potential to provide an important tool to control transmission of infectious diseases transmitted to the human population by these insects. One option is to have transgenes that will prevent pathogen transmission linked to other transgenes that confer a selective advantage to the transgenic mosquito strain in terms of reproductive fitness, pesticide and/or pathogen resistance.

A remaining challenge to these techniques, however, is the compromised reproductive fitness of the transgenic insects caused by the specific transgenes they harbor. Hence, there is a need for female-specific promoter/enhancer elements to generate female-specific expression. Ideally, the expression system would direct expression in female fat bodies at a late stage of insect larval development, as expression of transgenes in the fat body of female insects could confer greater fertility and fecundity to transgenic insects.

SUMMARY OF THE INVENTION

One aspect of the present invention encompasses an insect expression system comprising: (a) an enhancer element comprising a nucleic acid sequence that hybridizes under stringent conditions to all or a portion of a nucleic acid sequence comprising SEQ ID NO:1; (b) a promoter operably linked to the enhancer element of (a); (c) one or more heterologous nucleic acid sequences for expression in the insect operably linked to the promoter in (b); wherein, the enhancer element directs female-specific expression of the heterologous nucleic acid sequence at a level greater than six fold higher in female than in male insects.

In another aspect of the invention, the invention encompasses a transgenic insect comprising an expression system, the expression system comprising: (a) an enhancer element comprising a nucleic acid sequence that hybridizes under stringent conditions to all or a portion of a nucleic acid sequence comprising SEQ ID NO:1; (b) a promoter operably linked to the enhancer element of (a); (c) one or more heterologous nucleic acid sequences for expression in the insect operably linked to the promoter in (b); wherein, the enhancer element directs female-specific expression of the heterologous nucleic acid sequence at a level greater than six fold higher in female than in male insects.

In yet another aspect, the invention encompasses a method for genetically modifying a target insect population, the method comprising: (a) providing a transgenic insect comprising an expression system, the expression system comprising: (i) an enhancer element comprising a nucleic acid sequence that hybridizes under stringent conditions to all or a portion of a nucleic acid sequence comprising SEQ ID NO:1; (ii) a promoter operably linked to the enhancer element of (i); (iii) one or more heterologous nucleic acid sequences for expression in the insect operably linked to the promoter in (ii); wherein, the enhancer element directs female-specific expression of the heterologous nucleic acid sequence at a level greater than six fold higher in female than in male insects, and (b) introducing the genetically modified insect into the target population.

Other aspects and iterations of the invention are described more thoroughly below.

REFERENCE TO COLOR FIGURES

The patent or application file contains at least one drawing executed in color. Copies of this patent or patent application publication with color drawing(s) will be provided by the Office upon request and payment of the necessary fee.

DETAILED DESCRIPTION OF THE INVENTION

The present invention provides an insect expression system that directs female-specific expression in insects. Surprisingly, the inventors discovered that the insect expression system of the invention directs female-specific expression of a heterologous nucleic acid sequence at a level greater than six fold higher in female than in male insects. The invention also provides for transgenic insects comprising the expression system, and a method for genetically modifying a target insect population. Each of these embodiments is discussed in more detail below.

The invention may be used to provide biological control of pest insects and control transmission of infectious diseases transmitted to the human population by insects. Advantageously, the insect expression system of the invention directs expression of heterologous sequences in the female fat body during the late larval stage of the insect. These characteristics make the expression system of the invention ideal for controlling pest insect populations and the infectious diseases they transmit.

I. Insect Expression System

One aspect of the invention encompasses an insect expression system comprising an enhancer element operably linked to a promoter, which in turn is operably linked to a heterologous nucleic acid sequence for expression in the insect, wherein the enhancer element directs female-specific expression of the heterologous nucleic acid sequence at a level greater than six fold higher in female than in male insects.

The insect expression system and female-specific expression directed by the expression system of the invention are discussed in more detail below.

(a) Enhancer Element

The present invention encompasses an insect expression system comprising an enhancer element. An enhancer element, as used herein, refers to a nucleic acid segment capable of being operably linked to a promoter to induce transcription of the promoter. The enhancer element of the invention comprises a nucleic acid sequence that hybridizes under stringent conditions to all or a portion of a nucleic acid comprising SEQ ID NO:1. In one embodiment, the enhancer element comprise a nucleic acid sequence that hybridizes under stringent conditions to all or a portion of a nucleic acid comprising SEQ ID NO:2. In another embodiment, the enhancer element comprise a nucleic acid sequence that hybridizes under stringent conditions to all or a portion of a nucleic acid comprising SEQ ID NO:3.

Figure 1:
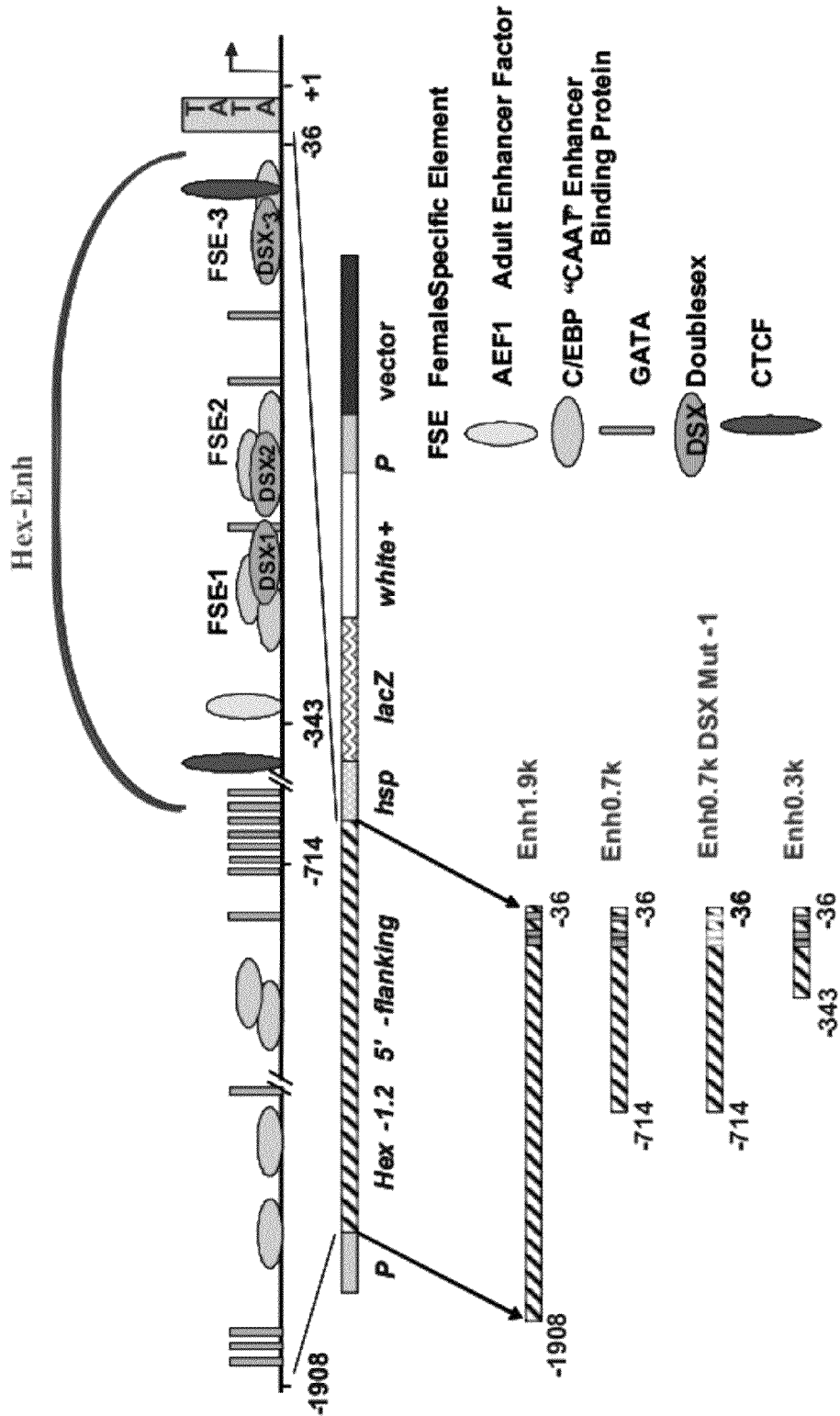
FIG. 1 depicts a map of constructs used to dissect regulatory domains in the Hexamerin 1.2 5'-flanking region. Three fragments from the Hexamerin1.2 5' flanking region were used to generate fusion genes with the hsp70 basal promoter and the lacZ reporter, which encodes β-galactosidase (β-gal). Putative transcription factor binding sites are shown.

In an exemplary embodiment, the enhancer element comprises a nucleic acid sequence that hybridizes under stringent conditions to all or a portion of a SEQ ID NO:1 comprising a female specific element (see FIG. 1). A female specific element typically comprises a Doublesex binding site.

Hybridization conditions corresponding to particular degrees of stringency vary depending upon the nature of the hybridization method of choice and the composition and length of the hybridizing DNA used. Generally, the temperature of hybridization and the ionic strength (especially the sodium ion concentration) of the hybridization buffer will determine the stringency of hybridization. Calculations regarding hybridization conditions required for attaining particular degrees of stringency are discussed by Sambrook et al. (1989). In Molecular Cloning: A Laboratory Manual, Cold Spring Harbor, N.Y., chapters 9 and 11, herein incorporated by reference.

In some embodiments of the present invention, stringent conditions may be defined as those under which the nucleic acid sequence is at least 50% identical to a nucleic acid sequence comprising SEQ ID NO:1, 2, 3, or a portion thereof. In other embodiments of the present invention, stringent conditions may be defined as those under which the nucleic acid sequence is at least 60% identical to a nucleic acid comprising SEQ ID NO:1, 2, 3, or a portion thereof. In yet other embodiments of the present invention, stringent conditions may be defined as those under which the nucleic acid sequence is at least 70% identical to a nucleic acid sequence comprising SEQ ID NO:1, 2, 3, or a portion thereof. In other embodiments of the present invention, stringent conditions may be defined as those under which the nucleic acid sequence is at least 80% identical to a nucleic acid sequence comprising SEQ ID NO:1, 2, 3, or a portion thereof. In additional embodiments of the present invention, stringent conditions may be defined as those under which the nucleic acid sequence is at least 90% identical to a nucleic acid sequence comprising SEQ ID NO:1, 2, 3, or a portion thereof. In preferred embodiments of the present invention, stringent conditions may be defined as those under which the nucleic acid sequence is at least 95% identical to a nucleic acid sequence comprising SEQ ID NO:1, 2, 3, or a portion thereof. In exemplary embodiments, stringent conditions may be defined as those under which the nucleic acid sequence is at least 100% identical to a nucleic acid sequence comprising SEQ ID NO:1, 2, 3, or a portion thereof. In a further embodiment, stringent conditions may be defined as those under which the nucleic acid sequence is at least 75, 76, 77, 78, 79, 80, 81, 82, 83, 84, 85, 86, 87, 88, 89, 90, 91, 92, 93, 94, 95, 96, 97, 98, 99, or 100% identical to a nucleic acid sequence comprising SEQ ID NO:1, 2, 3, or a portion thereof. In each of the above embodiments, the portions of SEQ ID NO:1, SEQ ID NO:2, or SEQ ID NO:3 typically comprise at least one female specific element (see FIG. 1).

Determining percent identity may be determined by conventional algorithms, which typically allow introduction of a small number of gaps in order to achieve the best fit. In particular, "percent identity" of two nucleic acid sequences is determined using the algorithm of Karlin and Altschul [(Proc. Natl. Acad. Sci. USA 87, 2264 (1993)]. Such an algorithm is incorporated into the NBLAST program of Altschul, et al. (J. Mol. Biol. 215, 403 (1990)). BLAST nucleotide searches may be performed with the NBLAST program to obtain nucleotide sequences homologous to a nucleic acid molecule of the invention. To obtain gapped alignments for comparison purposes, Gapped BLAST is utilized as described in Altschul, et al. (Nucleic Acids Res. 25, 3389 (1997)). When utilizing BLAST and Gapped BLAST programs, the default parameters of the respective programs (e.g., XBLAST and NBLAST) are employed. See www.ncbi.nlm.nih.gov for more details.

In some embodiments, the enhancer element of the invention comprises a nucleic acid sequence that hybridizes under stringent conditions to a portion of a nucleic acid comprising SEQ ID NO:1. In an alternative of the embodiments, the enhancer element of the invention comprises a nucleic acid sequence that hybridizes under stringent conditions to a nucleic acid comprising SEQ ID NO:2. In another alternative of the embodiments, the enhancer element of the invention comprises a nucleic acid sequence that hybridizes under stringent conditions to a nucleic acid comprising SEQ ID NO:3.

For each of the foregoing embodiments, the nucleic acid sequence of the enhancer element may be mutated to produce SEQ ID NO:4, 5 and 6. SEQ ID NO:4, 5, or 6 comprise mutations in the doublesex binding site that comprises a female specific element (see FIG. 1). In some embodiments, the enhancer element of the invention comprises a nucleic acid sequence that hybridizes under stringent conditions to a portion of a nucleic acid comprising SEQ ID NO:4. In an alternative of the embodiments, the enhancer element of the invention comprises a nucleic acid sequence that hybridizes under stringent conditions to a nucleic acid comprising SEQ ID NO:5. In another alternative of the embodiments, the enhancer element of the invention comprises a nucleic acid sequence that hybridizes under stringent conditions to a nucleic acid comprising SEQ ID NO:6.

(b) Promoter

In some embodiments, the enhancer element is operably linked to a promoter. The term promoter, as used herein, may mean a synthetic or naturally-derived molecule which is capable of conferring or activating expression of a target nucleic acid sequence in a cell. The promoter and target sequence may be the promoter normally associated with the enhancer element of the invention, or may be a heterologous promoter. A heterologous promoter may be derived from such sources as viruses, bacteria, fungi, plants, insects, and animals. A promoter may regulate the expression of a nucleic acid sequence constitutively or differentially with respect to the cell, the tissue or organ in which expression occurs or, with respect to the developmental stage at which expression occurs, or in response to external stimuli such as physiological stresses, pathogens, metal ions, or inducing agents or activators (i.e. an inducible promoter). For instance, the promoter may be inactive in the presence or absence of the activator. Similarly, the activity of the promoter may increase or decrease with an increasing concentration of the activator. Non-limiting representative examples of promoters may include the bacteriophage T7 promoter, bacteriophage T3 promoter, SP6 promoter, HSP70 basal promoter, lac operator-promoter, tac promoter, SV40 late promoter, SV40 early promoter, RSV-LTR promoter, the polyubiquitin promoter (*Drosophila melanogaster*), CMV IE promoter, a promoter comprising the tetracycline response element (TRE) nucleic acid sequence, and the CMV IE promoter.

In some embodiments, the promoter is the promoter normally associated with the enhancer element of the invention. In other embodiments, the promoter is the HSP70 basal promoter. In preferred embodiments, the promoter is an inducible promoter capable of regulating the expression of the heterologous nucleic acid differentially in response to an externally supplied activator. Suitable promoter-activator systems may include promoters that respond differentially to an antibiotic. For instance, an activator may be tetracycline, a streptogramin (for instance, erythromin), a tetracycline (for instance Doxycycline) or a macrolide (for instance, pristinamycin). In some embodiments, the inducible promoter is a promoter described in Biotechnology and Bioengineering (2003) 83(7):810-820 hereby incorporated by reference in its entirety. In an exemplary embodiment, the promoter is a promoter comprising the tetracycline-responsive TRE nucleic acid sequence capable of differentially regulating the expression of a heterologous nucleic acid in response to tetracycline or derivatives of tetracycline.

(c) Heterologous Nucleic Acid

The promoter of the invention is operably linked to a heterologous nucleic acid sequence. Generally speaking, the promoter directs transcription of the heterologous nucleic acid sequence. Possible heterologous sequences are discussed in more detail below, but may include non-coding sequences (e.g. for purposes of down-regulation of target nucleic acid sequences) or coding sequences comprising an open reading frame having at least one exon of a protein coding sequence.

In some embodiments, the heterologous sequence expresses more than one nucleic acid or polypeptide. For instance, in some embodiments, the heterologous nucleic acid expresses more than one protein. For example, in one embodiment, more than one protein may be expressed as a single fusion polypeptide. In another embodiment, more than one protein may be expressed as a single fusion polypeptide which is cleaved into the individual polypeptides after translation. By way of non-limiting example, 2A peptides of picornaviruses inserted between polypeptides comprising a fusion protein may result in the co-translational 'cleavage' of the proteins and lead to expression of multiple proteins at equimolar levels. In another alternative, the heterologous nucleic acid may express a polycystronic transcript that is translated into separate proteins. As would be recognized in the art, such polycystronic expression in eukryotic cells may be achieved through internal ribosomal entry sites (IRES) for translation of an internal open reading frame. IRES elements allow a cap-independent translation mechanism in which an IRES element positioned 3' downstream of the open reading frame translated from the cap region of the mRNA is recognized by the ribosome, allowing translation of a second coding region from the transcript. IRES elements from virus and mammalian messages have been described. Non-limiting examples of IRES elements that may be used in the invention include IRES elements from poliovirus Type I, the 5'UTR of encephalomyocarditis virus (EMV), of Thelier's murine encephalomyelitis virus (TMEV), of foot and mouth disease virus (FMDV), of bovine enterovirus (BEV), of coxsackie B virus (CBV), of human rhinovirus(HRV), the human immunoglobulin heavy chain binding protein (BIP) 5'UTR, the *Drosophila* antennapediae 5'UTR, the *Drosophila* ultrabithorax 5'UTR, or genetic hybrids or fragments from the above. In preferred embodiments, the heterologous nucleic acid expresses a monocystronic transcript.

In some embodiments, the heterologous nucleic acid sequence may encode a reporter. As used herein, a reporter refers to a biomolecule that may be used as an indicator of transcription through a particular promoter. Suitable reporters are known in the art. Non-limiting examples of reporters may include visual reporters or selectable-marker reporters. Visual reporters typically result in a visual signal, such as a color change in the cell, or fluorescence or luminescence of the cell. For instance, the reporter LacZ, which encodes β-galactosidase, will turn a cell blue in the presence of a suitable substrate, such as X-gal. Alternatively, a fluorescent protein may be used, such as GFP, yellow fluorescent protein (e.g. YFP, Citrine, Venus, YPet), blue fluorescent protein (e.g. EBFP, EBFP2, Azurite, mKalama1), cyan fluorescent protein (e.g. ECFP, Cerulean, CyPet), or other suitable fluorescent protein. Additionally, luciferase may be used. Selectable-marker reporters typically confer a selectable trait to the cell, such as drug resistance (e.g. antibiotic resistance). In some preferred embodiments, the heterologous nucleic acid sequence of the invention encodes β-galactosidase.

In other embodiments, the heterologous nucleic acid may encode an effector. An effector may be any genetic element which is capable of imparting a desired phenotype to the insect upon expression in the insect. Non-limiting examples of desirable effectors may be death factors, factors that impart resistance to a disease, factors that impart resistance to the ability to carry a disease, factors that enhance the survival of the host under certain conditions, or combinations thereof.

In preferred embodiments, the effector may be a death factor. A death factor as used herein is an element capable of exerting a lethal effect upon the insect when expressed in the insect. A wide range of suitable death factors with varying toxicities are known in the art. By way of non-limiting example, dominant mutant forms of cell-signaling or cell-cycle genes are appropriate for use in the present invention. Constructs which result in overexpression of such genes may also be lethal. Similarly constructs which result in inadequate expression of any essential gene would also be lethal. This might be achieved by expression of an inhibitory sequence, for example antisense RNA, sense RNA (acting by gene silencing), double stranded RNA ("inhibitory RNA" or RNAi) or other inhibitory RNA molecule. Overexpression of protein inhibitors of essential functions could also perform this lethal function. Other suitable targets for engineering constructs may include factors which disrupt metabolism or regulation of the cell to a fatal extent, such as disruption or overexpression of extracellular signaling factors such as functional homologues of Wnt, Shh or TGFβ. Other possibilities for death factors include sex-determination genes which may act to transform the sex of the organism. In this case, transformation of females to sterile males would also enable biological control, and the lethal gene is lethal to the population as such and not specifically to the organism.

Pro-drug-converting enzymes may also be used. A pro-drug is a drug, often a potentially toxic drug, which is selectively activated, i.e. rendered toxic, by the action of a pro-drug converting enzyme. Pro-drug converting enzymes, also known as "suicide" genes are harmless when expressed in an organism in the absence of the pro-drug substrate, which is not present in a normal host. However, when a non-toxic substrate is added, the pro-drug can activate the substrate and turn it into a toxic compound that would kill the host. Enzyme/pro-drug systems are known in the art. One common enzyme/pro-drug system is the 5-fluorouracil/cytosine deaminase system, in which the non-toxic precursor 5-fluorocytosine (5-FC) is converted to the cytotoxic drug 5-fluorouracil (5-FU) by the action of cytosine deaminase. Other examples include the esterase enzyme which converts DPX-JW062 into its active metabolite.

In other embodiments, the effector might provide a selective advantage to the insect. The organisms may be further modified by providing for a competitive advantage against other wild-type microorganisms in the field. By way of non-limiting example, an effector that may provide a selective advantage may be an effector that imparts resistance to malaria to the mosquito. Mosquitoes that were genetically engineered to be resistant to malaria were shown to be more fit than non-genetically modified control mosquitoes when feeding on mice infected with malaria.

(d) Expression System

As would be recognized in the art, the enhancer element may function in either orientation and in any location (upstream or downstream) relative to the promoter. The promoter of the expression system may be positioned 5' (upstream) or 3' (downstream) of a nucleic acid under its control. The distance between the promoter and a gene may be approximately the same as the distance between that promoter and the nucleic acid it controls in the gene from which the promoter is derived. As is known in the art, variation in this distance may be accommodated without loss of promoter function. In some embodiments, the enhancer element is 5' of, and operably linked to the promoter, and the promoter is 5' of, and operably linked to the heterologous nucleic acid sequence.

In some embodiments, the expression system further comprises a transcription termination sequence. A transcription termination sequence may be included to prevent inappropriate expression of nucleic acid sequences adjacent to the heterologous nucleic acid sequence.

All the nucleic acid sequences of the invention may be obtained using a variety of different techniques known in the art. The nucleotide sequences, as well as homologous sequences, may be isolated using standard techniques, purchased or obtained from a depository. Once the nucleotide sequence is obtained, it may be amplified for use in a variety of applications, using methods known in the art.

In some embodiments, the expression system is incorporated into a vector. One of skill in the art would be able to construct a vector through standard recombinant techniques (see, for example, Sambrook et al., 2001 and Ausubel et al., 1996, both incorporated herein by reference). Vectors include but are not limited to, plasmids, cosmids, transposable elements, viruses (bacteriophage, animal viruses, and plant viruses), and artificial chromosomes (e.g., YACs), such as retroviral vectors (e.g. derived from Moloney murine leukemia virus vectors (MoMLV), MSCV, SFFV, MPSV, SNV etc), lentiviral vectors (e.g. derived from HIV-1, HIV-2, SIV, BIV, FIV etc.), adenoviral (Ad) vectors including replication competent, replication deficient and gutless forms thereof, adeno-associated viral (AAV) vectors, simian virus 40 (SV-40) vectors, bovine papilloma virus vectors, Epstein-Barr virus, herpes virus vectors, vaccinia virus vectors, Harvey murine sarcoma virus vectors, murine mammary tumor virus vectors, Rous sarcoma virus vectors.

(e) Female-Specific Expression

The enhancer element directs female-specific expression of the heterologous nucleic acid sequence. In some embodiments, the enhancer element directs female-specific expression of the heterologous nucleic acid sequence at a level at least 26 fold higher in female than in male insects. In other embodiments, the enhancer element directs female-specific expression of the heterologous nucleic acid sequence at a level at least 92 fold higher in female than in male insects. In yet other embodiments, the enhancer element directs female-specific expression of the heterologous nucleic acid sequence at a level at least 104 fold higher in female than in male insects. In other embodiments, the enhancer element directs female-specific expression of the heterologous nucleic acid sequence at a level at least 141 fold higher in female than in male insects. In still other embodiments, the enhancer element directs female-specific expression of the heterologous nucleic acid sequence at a level greater than 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or more than 100 fold higher in female than in male insects. In further embodiments, the enhancer element directs female-specific expression of the heterologous nucleic acid sequence at a level greater than 100, 105, 110, 115, 120, 125, 130, 135, 140, 145, 150, 155, 160, 165, 170, 175, 180, 185, 190, 195, or 200 fold higher in female than in male insects.

In some embodiments, the insect expression system further directs expression of the heterologous nucleic acid sequence in the fat body of the female insect. In some embodiments, the insect expression system further directs expression of the heterologous nucleic acid sequence at a late larval stage and early adult stage of insect development.

II. Transgenic Insects Comprising Expression System

In another aspect of the invention, the invention encompasses a transgenic insect comprising an expression system, the expression system comprising: (a) an enhancer element comprising a nucleic acid sequence that hybridizes under stringent conditions to all or a portion of a nucleic acid sequence comprising SEQ ID NO:1; (b) a promoter operably linked to the enhancer element of (a); (c) one or more heterologous nucleic acid sequences for expression in the insect operably linked to the promoter in (b); wherein, the enhancer element directs female-specific expression of the heterologous nucleic acid sequence at a level greater than six fold higher in female than in male insects. The expression system is as described in Section (I) above.

In some embodiments, the insect of the invention is a non-pest insect. By way of non-limiting example, the insect may be an insect used as a model organism in laboratory research. In some embodiments, the insect is a *Drosophila* sp. insect used as a model organism in a laboratory. In preferred embodiments, the insect of the invention is an insect pest. An insect pest may be either a direct or an indirect pest. Direct pests are those insects which cause damage at one or more stage of their life cycle by, for example, eating crops or damaging animals. Indirect pests are those insects which are vectors of human diseases, such as mosquitoes which carry malaria. Indirect pests of organisms other than humans, such as livestock or plants are also known. Non-limiting examples of insect pests may include, but are not limited to the cotton bollworm (*Heliothis armigera*); the cabbage looper (*Trichoplusa ni*); the tobacco hornworm (*Manduca sexta*); the grapevine moth (*Lobesia botrana*); the black fly (*Simulium* sp.); the sand fly (*Phlebotomus* sp.); the house fly (*Musca domestica*); the Australian sheep blowfly (*Lucilia cuprina*), Asian tiger mosquito (*Aedes albopictus*); Japanese beetle (*Popilla japonica*), White-fringed beetle (*Graphognatus* spp.), Citrus blackfly (*Aleurocanthus woglumi*), Oriental fruit fly (*Dacus dorsalis*), Olive fruit fly (*Dacus oleae*), tropical fruit fly (*Dacus cucurbitae, Dacus zonatus*), Mediterranean fruit fly (*Ceratitis capitata*), Natal fruit fly (*Ceratitis rosa*), Cherry fruit fly (*Rhagoletis cerasi*), Queensland fruit fly (*Bactrocera tryoni*), Caribbean fruit fly (*Anastrepha suspensa*), fire ants (*Solenopis richteri, Solenopis invicta*), Gypsy moth (*Lymantria dispar*), Codling moth (*Cydia pomonella*), Brown tail moth (*Euproctis chrysorrhoea*), yellow fever mosquito (*Aedes aegypti*), malaria mosquitoes (*Anopheles gambiae, Anopheles stephensi*), New world screwworm (*Cochliomyia hominivorax*), Old World Screwworm (*Chrysomya bezziana*), Tsetse fly (*Glossina* spp), Boll weevil (*Anthonomous grandis*), Damsel fly (*Enallagma hageni*), Dragonfly (*Libellula luctuosa*), and rice stem borer (*Tryporyza incertulas*). In a preferred embodiment, the insect is a mosquito. In an exemplary embodiment, the insect is the *Aedes aegypti* mosquito.

Generation of a transgenic insect may be performed using any technique known in the art suitable for the particular insect of interest. Non-limiting examples of art recognized techniques may include DNA transfection using transposons, the use of viral vectors, and the use of episomal vectors which are transmitted through germ cells. By way of non-limiting examples, transgenic *Drosophila* flies may be generated using transfection of transposable P-element vectors comprising the insect expression system of the invention into flies according to Rubin et al. in *Science* 1982; 218:348:353, hereby incorporated by reference in its entirety. By way of another non-limiting example, transgenic mosquitoes may be generated using transfection of transposable element vectors comprising the insect expression system of the invention into mosquitoes according to Catterucia et al. in *Nature* 2000; 405:959:962 and Ito et al. in *Nature* 2002; 417:452-455, all of which are hereby incorporated by reference in their entirety. By way of yet another non-limiting example, transgenic Medflies may be generated using transfection of the transposable element Minos vectors comprising the insect expression system of the invention into flies according to U.S. Pat. No. 5,840,865, which is incorporated herein by reference in its entirety. By way of another non-limiting example, transgenic houseflies may be generated using transfection of the transposable element Hermes vectors comprising the insect expression system of the invention into flies according to U.S. Pat. No. 5,614,398, which is incorporated herein by reference in its entirety.

In some embodiments, the transgenic insect further comprises an expression cassette. As used herein, an "expression cassette" is a nucleic acid construct comprising a nucleic acid sequence for expression in the insect operably linked to a promoter. In some embodiments, the expression system further comprises a transcription termination sequence. The nucleic acid sequence, the promoter and the termination sequence of the expression cassette are as described in Section (I) above. In preferred embodiments, the expression cassette encodes the tetracycline-repressible transcriptional activator (tTA) protein.

In an exemplary embodiment, the transgenic insect comprises an expression system wherein the enhancer element is a nucleic acid sequence that hybridizes under stringent conditions to a nucleic acid selected from the group comprising SEQ ID NO:1, 2, 3 or a portion thereof, the promoter is the hsp70 basal promoter, and the heterologous nucleic acid of the expression system encodes β-galactosidase.

In another exemplary embodiment, the transgenic insect comprises an expression system and an expression cassette wherein the expression system comprises an enhancer element comprising a sequence that hybridizes under stringent conditions to a nucleic acid selected from the group comprising SEQ ID NO:1, 2, 3 or a portion thereof, the promoter is a promoter comprising the tetracycline-responsive TRE nucleic acid sequence capable of differentially regulating the expression of a heterologous nucleic acid in response to tetracycline or derivatives of tetracycline, and the heterologous nucleic acid of the expression system encodes a death factor, and the expression cassette encodes the tetracycline-repressible transcriptional activator (tTA) protein.

III. Methods of Using

In yet another aspect, the invention encompasses a method for genetically modifying a target insect population, the method comprising: (a) providing a transgenic insect comprising an expression system, the expression system comprising: (i) an enhancer element comprising a nucleic acid sequence that hybridizes under stringent conditions to all or a portion of a nucleic acid sequence comprising SEQ ID NO:1; (ii) a promoter operably linked to the enhancer element of (i); (iii) one or more heterologous nucleic acid sequences for expression in the insect operably linked to the promoter in (ii); wherein, the enhancer element directs female-specific expression of the heterologous nucleic acid sequence at a level greater than six fold higher in female than in male insects, and (b) introducing the genetically modified insect into the target population. In some embodiments, the transgenic insect further comprises an expression cassette. The insect expression system, the expression cassette and the transgenic insect are as described above.

In some embodiments, the transgenic insects are introduced into the target population. The transgenic insects of the invention will consequently interbreed with the wild-type populations to produce target insects genetically modified to contain the expression system of the invention. Depending on the target insect and on the target genetic modification of the insect population, male, female or both transgenic insects may be released. In some embodiments, male and female transgenic insects are released. In other embodiments, only male insects are released. In yet other embodiments, only female insects are released.

In preferred embodiments, the target insect population is a mosquito population, the transgenic insect comprises an expression system and an expression cassette wherein, the expression system comprises an enhancer element comprising a nucleic acid sequence that hybridizes under stringent conditions to all or a portion of a nucleic acid sequence selected from the group comprising SEQ ID NO:1, 2 or 3, the promoter is a promoter comprising the tetracycline-responsive TRE nucleic acid sequence capable of differentially regulating the expression of a heterologous nucleic acid in response to tetracycline or derivatives of tetracycline, and the heterologous nucleic acid of the expression system encodes a death factor, and the expression cassette encodes the tetracycline-repressible transcriptional activator (tTA) protein, and only male mosquitoes are released as described in Example 3 below.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise.

"Enhancer element" refers to a nucleic acid segment capable of being operably linked to a promoter to induce transcription of the promoter.

"Promoter" refers to a synthetic or naturally-derived molecule which is capable of conferring or activating expression of a nucleic acid in a cell.

"Heterologous nucleic acid sequence" refers to a nucleic acid sequence not normally operably linked to the promoter, or not normally expressed in the cell of interest.

EXAMPLES

The following examples illustrate various iterations of the invention.

Example 1

Female-Specific Expression Directed by the Hex-Enh Nucleic Acid Sequence

An enhancer element (Hex-Enh) was mapped to specific nucleic acid sequences in the 5'-flanking regions of the Hexamerin-1.2 gene of the mosquito, Aedes atropalpus (see FIG. 1 for Hex-Enh structure). The Hex-Enh enhancer element directs female-specific, stage-specific and tissue-specific expression in insects. Previously, it was shown that these sequences confer limited—two to six fold—female specificity and clear tissue specificity to reporter gene activity in a heterologous species, the fruit fly Drosophila melanogaster. The same Hex-Enh sequences were then tested in transgenic lines of the mosquito, Aedes aegypti.

Figure 2A:
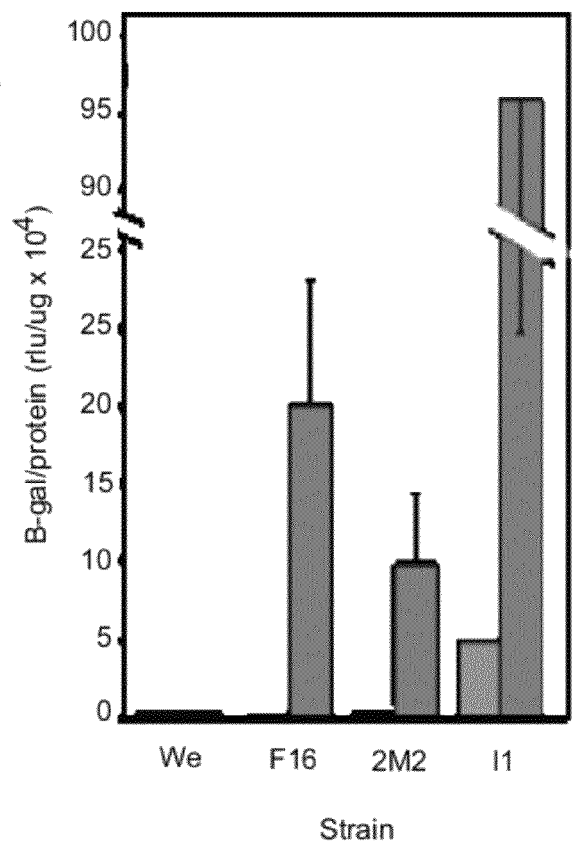
FIG. 2 depicts female-specific lacZ expression in transgenic *Aedes aegypti* mosquitoes. Three transgenic lines (F16, I1 and 2M2) and the host strain, We, were assayed for the level of β-gal enzyme activity. (A) β-gal activity in adult mosquitoes. Activity in 5-7-day old males and females is shown. (B) β-gal activity in L4 larvae. Activity in male and female L4 larvae is shown. (C) β-gal activity in older adult mosquitoes. Activity in L3 larvae and in 5-day, 10-day and older females is shown.
Figure 2B:
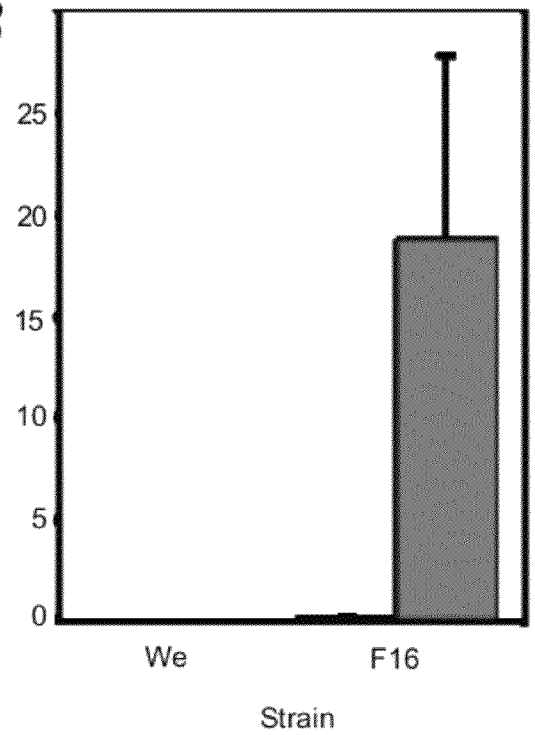

To that end, portions of the 5'-flanking regions of the Hex-1.2 gene were isolated and operably linked to the hsp70 basal promoter and the lacZ reporter to generate lacZ expression constructs controlled by the Hex-Enh regulator (FIG. 1). A first construct comprised positions −1908 to −36 (relative to the Hexamerin 1.2 transcription start site) of the Hex-1.2 gene. A second construct comprised positions −714 to −36 of the Hex-1.2 gene. A third construct comprised positions −714 to −36 of the Hex-1.2 gene, but also comprised a mutation in the triple binding sites of the DSX transcription factor. A fourth construct comprised positions −343 to −36 of the Hex-1.2 gene. Transgenic Aedes aegypti comprising the second construct, with positions −714 to −36 of the Hex-1.2 gene, were then generated.

β-gal activity driven by Hex-Enh was then measured in 5-7 day-old adult male and female mosquitoes (FIG. 2A). Very high female-specific expression of Hex-Enh directed B-gal expression was obtained in these adult mosquitoes. Surprisingly, expression in female adults was 26- to 140-fold higher in females than in males. Similar results were observed in L3 larvae, where females expressed 92-fold higher expression than males (FIG. 2B). These results are surprising, especially when compared to the previously-observed 2-6 fold higher levels of expression in female vs. male Drosophila transgenic insects expressing β-gal under the control of the same Hex-Enh enhancer element.

Figure 2C:
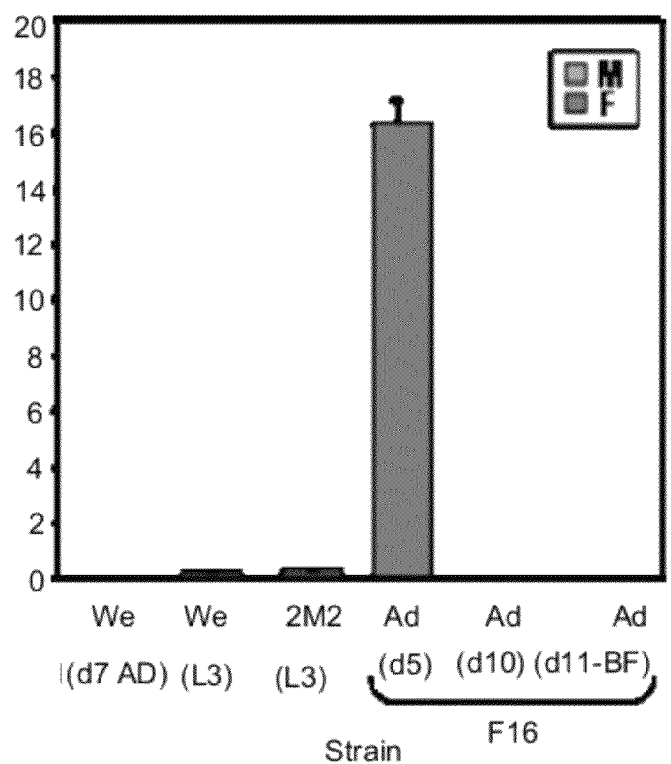

The expression was specific to the late larval stage L4 and early adults. There was no β-gal expression either in L3 larvae or in adults that are 10-days old or older (FIG. 2C).

Example 2

Tissue-Specific Expression Directed by the Hex-Enh Nucleic Acid Sequence

Figure 3A:
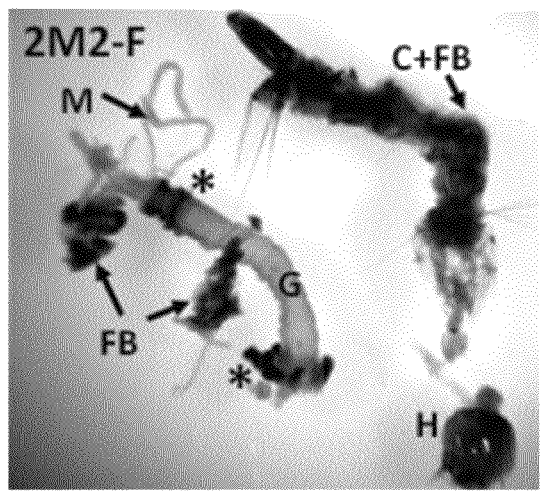
FIG. 3 depicts tissue-specific lacZ expression in transgenic *Aedes aegypti* mosquitoes. Female (F) and male (M) L4 larvae from three transgenic lines (F16(B), I1 (C) and 2M2 (A, D)) and the host strain, We (E), were stained for β-gal reporter enzyme activity. C, cuticle with trachea; FB, fat body; G, gut; H, head; M, Malpighian tubules; *ectopic expression.
Figure 3B:
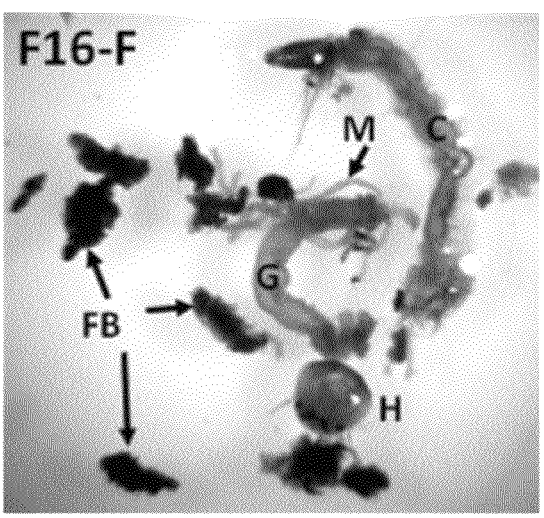
Figure 3C:
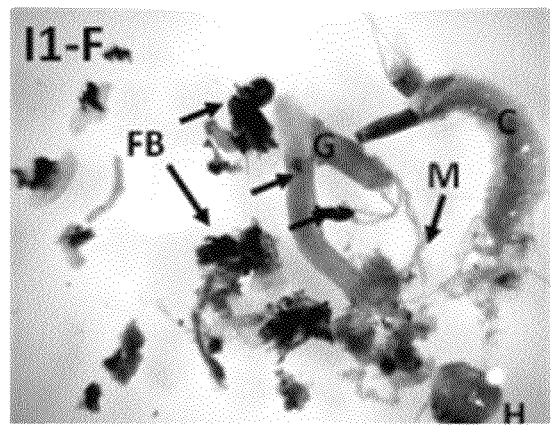
Figure 4:
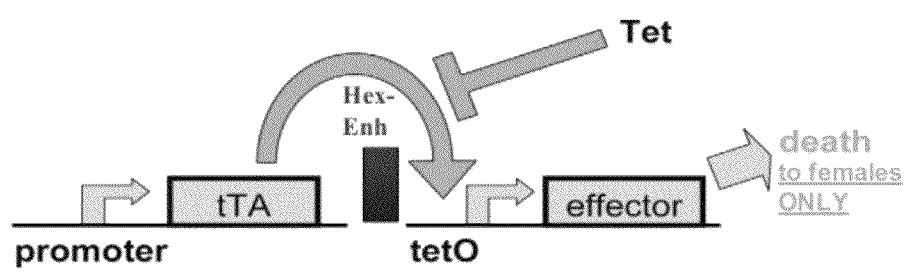
FIG. 4 depicts the use of tTA and the tetracycline-repressible expression system to obtain killing of female mosquitoes. The tetracycline-repressible transcriptional activator (tTA) protein is placed under the control of the promoter/enhancer of choice. When expressed (in the absence of tetracycline, Tet), the tTA protein binds to the tetO sequence, driving expression of the effector gene. However, in the presence of low Tet concentrations, the tTA protein does not bind the tetO sequence; and expression of the effector gene is repressed.

The transgenic mosquitoes described in Example 1 above also exhibited tissue-specific β-gal expression (FIG. 3). Male and female mosquito L4 larvae from the host strain and the three transgenic lines were stained for β-gal reporter gene activity. The expression was clearly targeted to the fat body or liver of the mosquito.

Example 3

Use of the Insect Expression System for Mosquito Population Control

The expression system of the invention may be used in a variation of the RIDL system (Alphey et al., 2002, Insect Biochem Mol Biol 32:1243-1247) to generate male-only mosquitoes for release into a wild population for the biological control of mosquitoes.

To that end, transgenic mosquitoes may be generated. The transgenic mosquitoes may comprise the expression system of the invention and an expression cassette wherein, the expression system comprises an enhancer element comprising a sequence that hybridizes under stringent conditions to all or a portion of a nucleic acid sequence comprising a sequence comprising all of a portion of a nucleic acid sequence comprising SEQ ID NO:1, 2 or 3, the promoter is a promoter comprising the tetracycline-responsive TRE nucleic acid sequence capable of differentially regulating the expression of a heterologous nucleic acid in response to tetracycline or derivatives of tetracycline, and the heterologous nucleic acid of the expression system encodes a death factor, and the expression cassette encodes the tetracycline-repressible transcriptional activator (tTA) protein.

Transgenic mosquitoes may be grown under controlled conditions in the presence of tetracycline. Tetracycline may be fed to the mosquitoes by incorporation into the mosquito diet. In the transgenic mosquito, tetracycline binds the tTA transcriptional activator and renders it incapable of binding to tetracycline response element (TRE) sequences, therefore preventing transactivation of the death factor, and allowing females to breed in order to propagate the transgenic insects. Shortly before release of the insects into the wild target population, tetracycline may be removed from the controlled population allowing tTA to bind TRE sequences and transactivation of the death factor. Since the expression system also comprises the enhancer element that directs female-specific expression, the death factor may be expressed only in females, leading to the death of females, and allowing the efficient production of a male-only transgenic insect population for release. These males are then released in large numbers into the affected region. Upon release, the males may compete with wild type males of the target population for female insects for mating. The released males are not sterile, but any female offspring their mates produce will express the death factor, and so will die. The number of females in the wild population will therefore decline, causing the overall population to decline. Using this method, the males may not have to be sterilized by radiation before release, making the males healthier and better able to compete with the wild male population for mates.

What is claimed is:

1. An expression system comprising:
   (a) an enhancer sequence consisting of SEQ ID NO: 1;
   (b) a heterologous promoter operably linked to the enhancer element of (a);
   (c) one or more heterologous nucleic acid sequences for expression in a mosquito operably linked to the promoter in (b);
   wherein, the enhancer element directs female-specific expression of the heterologous nucleic acid sequence at a level greater than six fold higher in female than in male mosquitoes.

2. The expression system of claim 1, wherein the heterologous nucleic acid is selected from the group consisting of nucleic acids encoding a transactivation factor, a reporter, and an effector.

3. The expression system of claim 2, wherein the effector is a cell death factor or a factor that provides a selective advantage to the mosquito.

4. The expression system of claim 1, wherein the enhancer element further directs expression of the heterologous nucleic acid sequence in the fat body of the female mosquito.

5. The expression system of claim 1, wherein the enhancer element further directs expression of the heterologous nucleic acid sequence at a late larval stage and early adult stage of mosquito development.

6. The insect expression system of claim 1, wherein the expression system is incorporated into a vector.

7. The expression system of claim 1, wherein the female-specific expression of the heterologous nucleic acid sequence is at a level greater than 10 fold higher in female than in male mosquitoes.

8. The expression system of claim 1, wherein the female-specific expression of the heterologous nucleic acid sequence is at a level greater than 25 fold higher in female than in male mosquitoes.

9. The expression system of claim 1, wherein the female-specific expression of the heterologous nucleic acid sequence is at a level greater than 100 fold higher in female than in male mosquitoes.

10. The expression system of claim 1, wherein the mosquitoes is the *Aedes aegypti* mosquito.

* * * * *

UNITED STATES PATENT AND TRADEMARK OFFICE
CERTIFICATE OF CORRECTION

| | | |
|---|---|---|
| PATENT NO. | : 8,263,397 B2 | Page 1 of 1 |
| APPLICATION NO. | : 12/722968 | |
| DATED | : September 11, 2012 | |
| INVENTOR(S) | : Helen Benes | |

It is certified that error appears in the above-identified patent and that said Letters Patent is hereby corrected as shown below:

IN THE CLAIMS:

Col. 20, line 48 (Claim 10, line 2): "mosquitoes" should read --mosquito--

Signed and Sealed this
Twentieth Day of November, 2012

David J. Kappos
*Director of the United States Patent and Trademark Office*

SEQUENCE LISTING

```
<160> NUMBER OF SEQ ID NOS: 6

<210> SEQ ID NO 1
<211> LENGTH: 1873
<212> TYPE: DNA
<213> ORGANISM: Aedes atropalpus

<400> SEQUENCE: 1
cgtatctgtt ctgcaccaac cggtgggagc ttggtcctgt acccatagtg atatagtgaa      60
cggaacatta tcaaatttgg agacaagtag atgcagatgt tatccaaaga atattggtta     120
acaccaggta gtcaatgaat taacatctgg tacctctcag ttcaaaacca agagacggac     180
cggaagacct gatgaaatta actgatcgca tgaaagctat acacatcaaa ctattagtac     240
gtcaaatttc atttaatttt acccaattta tcaaaagcta gtgcaatgtc agtgtgttca     300
gaaccacgtt ttatgaagag gaacaagacg tttttggatg cactcctcgc gataattttc     360
agtatcgatg gttcctgtcg taaaaactac agagcactct gtttaggcat tttccgcttc     420
ctcttagtct ttatcttgtt ccttcgcttg atattttgga cggctccaac ggacactctg     480
tttcacaaca aaaattcaaa acctttcttc tcgattttcg ggttcgcagg accacttttg     540
gatctggatc ttggcaaatc tttaacagta cagtgatctc caaatatttt gatgttttaa     600
acacagctga ctgcgatact ttcacaattt ttgcaatatc tcggcaagat attccctctt     660
cacattgttt tttaagaatc aaaccaatgg tttgaagatc agtttgctct cttttgtaaa     720
ttgaacacaa gaaactgaca atatttggta acaaactctt gtatactatg aaagttagtt     780
catcaaattt ggattaattg ttacatcaca acgtataggt gtcaacttta tacagtccgt     840
ttatacagtg atcagtcctt tattagaatg aacgccccc attccaagaa aggctgtgcc     900
cttgatctat gctaagaatc tttcctgtcc ttaaaagccc ctttatttca cgctaatcgg     960
cgtagtagtt gttcaatctt taaggctcag acagacagga aaacagacat acagaccgac    1020
agacagaagt ttatttttat agatattgat atatcttaaa tctatcggat gtttgactgg    1080
gaatatttag ataagtaaga cctactatta tttatgtcca attatttaca tttacaatta    1140
tttaattcat acattttgtt tcttttctag ttctttgaat acacataaga aaaatgcata    1200
aaaaagatat gactatcaag gatcgatagt tgagtgctaa gttgttatcg tgcttttagc    1260
gataagaaac cgtttcaatc aatcaaagca attcattcct attaattagt tacatttttc    1320
aataggccct ttagaaacat cacttgggat tcaacatgat gaactgatat caaatagtgg    1380
ctcttttatc aatgatagat acgattaaga tgttgttatt cttattttcc attaaatgcc    1440
tctgttttgg ttttatcaaa acgctgcact atggctttca aaaaatctgc tccctaccat    1500
```

```
tattttttt  gcttaaaatg  aataatttgt  cggaatttca  tagcatatcc  aatttaaatt    1560
ataagttcga  gcttatttca  gcattgaaga  gtcattgcac  accaaaactg  gcaagaaaca    1620
tatgttggag  cagcatcgca  ccgatgattg  caacttgcaa  ctttgtgctc  tgtgttatca    1680
ccgggtgaat  atactatgtt  tcaatttata  attgataatt  acctgcctgc  ctgccaataa    1740
ttcaccgtat  cgctctgact  tcaatagagc  aacagcacaa  gcgcttccaa  aatagcgacc    1800
ggcgactgat  aattcttaaa  tcagtagcca  cacgggtagg  cgataggggg  cagtgagatc    1860
gagaacattt  ttg                                                          1873

<210> SEQ ID NO 2
<211> LENGTH: 679
<212> TYPE: DNA
<213> ORGANISM: Aedes atropalpus

<400> SEQUENCE: 2
tgcataaaaa  agatatgact  atcaaggatc  gatagttgag  tgctaagttg  ttatcgtgct      60
tttagcgata  agaaaccgtt  tcaatcaatc  aaagcaattc  attcctatta  attagttaca     120
tttttcaata  ggccctttag  aaacatcact  tgggattcaa  catgatgaac  tgatatcaaa     180
tagtggctct  tttatcaatg  atagatacga  ttaagatgtt  gttattctta  ttttccatta     240
aatgcctctg  ttttggtttt  atcaaaacgc  tgcactatgg  ctttcaaaaa  atctgctccc     300
taccattatt  ttttttgctt  aaaatgaata  atttgtcgga  atttcatagc  atatccaatt     360
taaattataa  gttcgagctt  atttcagcat  tgaagagtca  ttgcacacca  aaactggcaa     420
gaaacatatg  ttggagcagc  atcgcaccga  tgattgcaac  ttgcaacttt  gtgctctgtg     480
ttatcaccgg  gtgaatatac  tatgtttcaa  tttataattg  ataattacct  gcctgcctgc     540
caataattca  ccgtatcgct  ctgacttcaa  tagagcaaca  gcacaagcgc  ttccaaaata     600
gcgaccggcg  actgataatt  cttaaatcag  tagccacacg  gtaggcgata  gggggcagt     660 gagatcgaga  acattttg                                                     679

<210> SEQ ID NO 3
<211> LENGTH: 308
<212> TYPE: DNA
<213> ORGANISM: Aedes atropalpus

<400> SEQUENCE: 3
ttcgagctta  tttcagcatt  gaagagtcat  tgcacaccaa  aactggcaag  aaacatatgt      60
tggagcagca  tcgcaccgat  gattgcaact  tgcaactttg  tgctctgtgt  tatcaccggg     120
tgaatatact  atgtttcaat  ttataattga  taattacctg  cctgcctgcc  aataattcac     180
cgtatcgctc  tgacttcaat  agagcaacag  cacaagcgct  tccaaaatag  cgaccggcga     240
ctgataattc  ttaaatcagt  agccacacgg  gtaggcgata  gggggcagtg  agatcgagaa     300
catttttg                                                                 308

<210> SEQ ID NO 4
<211> LENGTH: 1873
<212> TYPE: DNA
<213> ORGANISM: Aedes atropalpus

<400> SEQUENCE: 4
cgtatctgtt  ctgcaccaac  cggtgggagc  ttggtcctgt  acccatagtg  atatagtgaa      60
cggaacatta  tcaaatttgg  agacaagtag  atgcagatgt  tatccaaaga  atattggtta     120
acaccaggta  gtcaatgaat  taacatctgg  tacctctcag  ttcaaaacca  agagacggac     180
```

```
cggaagacct gatgaaatta actgatcgca tgaaagctat acacatcaaa ctattagtac      240
gtcaaatttc atttaatttt acccaattta tcaaaagcta gtgcaatgtc agtgtgttca      300
gaaccacgtt ttatgaagag gaacaagacg ttttttggatg cactcctcgc gataattttc    360
agtatcgatg gttcctgtcg taaaaactac agagcactct gtttaggcat tttccgcttc     420
ctcttagtct ttatcttgtt ccttcgcttg atattttgga cggctccaac ggacactctg     480
tttcacaaca aaaattcaaa acctttcttc tcgattttcg ggttcgcagg accacttttg     540
gatctggatc ttggcaaatc tttaacagta cagtgatctc caaatatttt gatgttttaa     600
acacagctga ctgcgatact ttcacaattt ttgcaatatc tcggcaagat attccctctt    660
cacattgttt tttaagaatc aaaccaatgg tttgaagatc agtttgctct cttttgtaaa    720
ttgaacacaa gaaactgaca atatttggta acaaactctt gtatactatg aaagttagtt    780
catcaaattt ggattaattg ttacatcaca acgtataggt gtcaaccttta tacagtccgt    840 ttatacagtg atcagtcctt tattagaatg aacgcccccc attccaagaa aggctgtgcc    900
cttgatctat gctaagaatc tttcctgtcc ttaaaagccc ctttatttca cgctaatcgg    960
cgtagtagtt gttcaatctt taaggctcag acagacagga aaacagacat acagaccgac    1020
agacagaagt ttatttttat agatattgat atatcttaaa tctatcggat gtttgactgg    1080
gaatatttag ataagtaaga cctactatta tttatgtcca attatttaca tttacaatta    1140
tttaattcat acattttgtt tcttttctag ttctttgaat acacataaga aaatgcata     1200 aaaagatat gactatcaag gatcgatagt tgagtgctaa gttgttatcg tgcttttagc     1260
gataagaaac cgtttcaatc aatcaaagca attcattcct attaattagt tacattttc     1320 aataggcct ttagaaacat cacttgggat tcaacatgat gaactgatat caaatagtgg     1380 ctctttatc aatgatagat acgattaaga tgttgttatt cttatttttcc attaaatgcc     1440 tctgttttgg ttttatcaaa acgctgcact atggctttca aaaaatctgc tccctaccat     1500 tattttttt gcttaaaatg aataatttgt cggaatttca tagcatatcc aatttaaatt     1560
ataagttcga gcttatttca gcattgaaga gtcattgcac accaaaactg gcaagaaaca     1620
tatgttggag cagcatcgca ccgatgattg caacttgcaa ctcatggctc tgtgttatca     1680
ccgggtgaat atcaggtgtt tcaatttata attgataatt acctgcctgc ctgccaataa     1740
ttcaccgtat cgctctgact tcaatagagc aacagcacaa gcgcttccaa aatagcgacc     1800
ggcgactgat aattcttaaa tcagtagcca cacgggtagg cgatagggggg cagtgagatc    1860 gagacaggtt ttg                                                        1873
```

<210> SEQ ID NO 5
<211> LENGTH: 679
<212> TYPE: DNA
<213> ORGANISM: Aedes atropalpus

<400> SEQUENCE: 5

```
tgcataaaaa agatatgact atcaaggatc gatagttgag tgctaagttg ttatcgtgct      60
tttagcgata agaaaccgtt tcaatcaatc aaagcaattc attcctatta attagttaca     120
tttttcaata ggccctttag aaacatcact tgggattcaa catgatgaac tgatatcaaa     180
tagtggctct tttatcaatg atagatacga ttaagatgtt gttattctta ttttccatta    240
aatgcctctg ttttggtttt atcaaaacgc tgcactatgg ctttcaaaaa atctgctccc    300
taccattatt ttttttgctt aaaatgaata atttgtcgga atttcatagc atatccaatt    360
taaattataa gttcgagctt atttcagcat tgaagagtca ttgcacacca aaactggcaa    420
```

-continued

```
gaaacatatg ttggagcagc atcgcaccga tgattgcaac ttgcaactca tggctctgtg      480
ttatcaccgg gtgaatatca ggtgtttcaa tttataattg ataattacct gcctgcctgc      540
caataattca ccgtatcgct ctgacttcaa tagagcaaca gcacaagcgc ttccaaaata      600
gcgaccggcg actgataatt cttaaatcag tagccacacg ggtaggcgat aggggcagt       660 gagatcgaga caggttttg                                                    679

<210> SEQ ID NO 6
<211> LENGTH: 308
<212> TYPE: DNA
<213> ORGANISM: Aedes atropalpus

<400> SEQUENCE: 6
ttcgagctta tttcagcatt gaagagtcat tgcacaccaa aactggcaag aaacatatgt       60
tggagcagca tcgcaccgat gattgcaact tgcaactcat ggctctgtgt tatcaccggg      120
tgaatatcag gtgtttcaat ttataattga taattacctg cctgcctgcc aataattcac      180
cgtatcgctc tgacttcaat agagcaacag cacaagcgct tccaaaatag cgaccggcga      240
ctgataattc ttaaatcagt agccacacgg gtaggcgata gggggcagtg agatcgagac      300
aggttttg                                                               308
```